United States Patent
Kreidler et al.

[11] Patent Number: 5,855,580
[45] Date of Patent: Jan. 5, 1999

[54] DISTRACTION DEVICE

[76] Inventors: Winfried Kreidler, Muhlsteigstrasse 15, D-78532 Tuttlingen; Konrad Wangerin, Thomasstrasse 45, D-70192 Stuttgart, both of Germany

[21] Appl. No.: 726,869

[22] Filed: Oct. 4, 1996

[30] Foreign Application Priority Data

Oct. 5, 1995 [DE] Germany ................ 195 37 023.6

[51] Int. Cl.⁶ .................................................. A61B 17/80
[52] U.S. Cl. ............................................. 606/71; 606/69
[58] Field of Search .............................. 606/71, 70, 69, 606/60, 72, 73, 57, 58, 90, 86, 105

[56] References Cited

U.S. PATENT DOCUMENTS

| | | | |
|---|---|---|---|
| 3,604,414 | 9/1971 | Borges | 606/105 |
| 4,187,841 | 2/1980 | Knutson | 606/105 |
| 4,929,247 | 5/1990 | Rayhack | 606/53 |
| 5,129,903 | 7/1992 | Luhr et al. | 606/71 |
| 5,364,396 | 11/1994 | Robinson et al. | 606/53 |
| 5,439,465 | 8/1995 | Tumibay | 606/105 |
| 5,681,313 | 10/1997 | Diez | 606/69 |
| 5,700,263 | 12/1997 | Schendel | 606/57 |

FOREIGN PATENT DOCUMENTS

4007306  5/1991  Germany ............................ 606/71

*Primary Examiner*—Guy V. Tucker

[57] ABSTRACT

The invention relates to a device for the distraction of at least two bone segments, with mountings which are displaceable relative to each other, for the distraction of bone segments in the jaw, face and skull region, in which the mounting (11) has an at least geometrical and at least essentially linear longitudinal axis (12), along which two complementary halves (13, 14) are adjustably movable by an adjustment device (41, 43, 16, 18; 82), and indeed with an increase of their mutual distance (63); the mounting (11) is essentially longer than it is wide, the halves are guided for longitudinal movement on each other by a guide (17, 31) which is secured against twisting, on each half (13, 14), at least one flat fixing device (23, 51) is provided, which can be fixed to the bone (56, 57) and which can take up thrust forces and torques, the adjusting device (41, 43, 16, 18; 82) is accessible at one place (36) for an adjusting member (42), which is essentially directed towards a bodily orifice, and outside the end region (34), a tool seat (87) is provided on the guide section (83).

39 Claims, 8 Drawing Sheets

Fig. 10

DISTRACTION DEVICE

BACKGROUND OF THE INVENTION

1. Field of the Invention

The invention relates to a device for the distraction of bone segments and more particularly to a device for distraction of bone segments in the jaw, face and skull region.

2. Discussion of Relevant Art

Such a device is disclosed in German Utility Model 94 01 911.8. This, and devices currently in use, have the disadvantage that they have to fitted on the bone segments from outside. This means that a rack device with numerous screws which are accessible from outside is located outside, for example, the jaw and on both sides of the ramus of the jaw. Fixation pins pass through the skin and are inserted into holes in the bone. The pins have a considerable length, so that, when the patient moves the rack device, their free ends stir around in the fixing holes with a great force. The retaining pins also have to be thin, since the wounds in the skin must not be too large: either for cosmetic reasons, or because large wounds are harder to take care of than small wounds. The retaining pins tend to bend. They are heavily stressed at times.

The known device is complicated to operate. It is also expensive to produce. Different devices have to be produced and held in storage, according to the size and shape of the jaw.

SUMMARY OF THE INVENTION

The invention has as its object to provide a device for the distraction of bone segments which makes possible an operation of an adjusting device without damaging tissue.

This object is attained, according to the invention, by a device for distraction of at least two bone segments, with mountings which are displaceable relative to each other, for the distraction of bone segments in the jaw, face and skull region. A mounting has an at least geometrical and at least substantially linear longitudinal axis, along which two complementary halves are adjustably movable by an adjusting device with an increase of their mutual distance. The mounting is longer than it is wide. The halves are guided for longitudinal movement on each other by a guide which is secured against twisting. On each half, at least one flat fixing device is provided, which can be fixed to a bone and which can take up thrust forces and torques. The adjusting device is accessible at a place for an adjusting member, which is directed towards a bodily orifice. The adjusting device on one half includes a sleeve with a free end region that is at least partially open, a guide section that is rotatably mounted in this end region, and outside the end region a tool seat arranged on the guide section.

BRIEF DESCRIPTION OF THE DRAWINGS

Preferred embodiment examples of the invention will now be described.

FIG. 2 shows a plan view of a second device, for the left jaw ramus, but seen from outside; FIGS. 1 and 2 are enlarged so that in their shortest state they are actually 62 mm long.

DETAILED DESCRIPTION OF PREFERRED EMBODIMENTS

A device 11 has a geometrical longitudinal axis 12, along which its two halves 13 and 14 are arranged. The half 13 includes a hexagonal rod 16, which has a regular external hexagonal body 17 which has a coaxial internal thread 16 that is open to the right in FIG. 3. The hexagonal rod 16 has on the left a tapered overlap 19, to which a shank 22, which extends along the geometrical longitudinal axis 12, of an angle piece 23 is fastened with its screw fastening end by two screws 21. Its other shank 24 projects vertically downwards. The one shank has two fastening holes 26; the other shank 24 has a fastening hole 27, and the two have in common a fastening hole 28. Fastening screws can be screwed through 26, 27 and 28, and can be screwed into the bone. The half 14 includes a coaxial external circular cylindrical sleeve 29, which has a coaxial internal hexagon 31 which guides the external hexagonal body 17 in the longitudinal direction, with little transverse play, and indeed over a distance which corresponds practically to its whole length, as can be gathered from a comparison of FIGS. 1 and 2, on one hand, with FIG. 3 on the other hand. The sleeve 29 has to the right an annular internal recess 32. A cap 34 is seated on its right-hand end face 33, and has a coaxial central hole 36 for the passage of a screwdriver blade. The cap 34 furthermore has an internal recess 37, so that together with the internal recess 32 a circular cylindrical internal space 38 results when the cap 34 is firmly connected to the right-hand end region of the sleeve 29. The coaxial head 41 of a threaded screw 42 can be freely rotated in the internal space 38 in the peripheral direction, because of the play which is present. The head 41 is held in the longitudinal direction with little play in the internal space 38 and cannot fall out, because the central hole 36 has a smaller diameter than the head 41. The threaded screw 42 has a shaft 43 which has an external thread 44 which engages with the internal thread 18. If the head 41 is turned in one direction, the hexagonal rod 16 is moved outwards. In the other direction, it is moved inwards.

Figure 3:
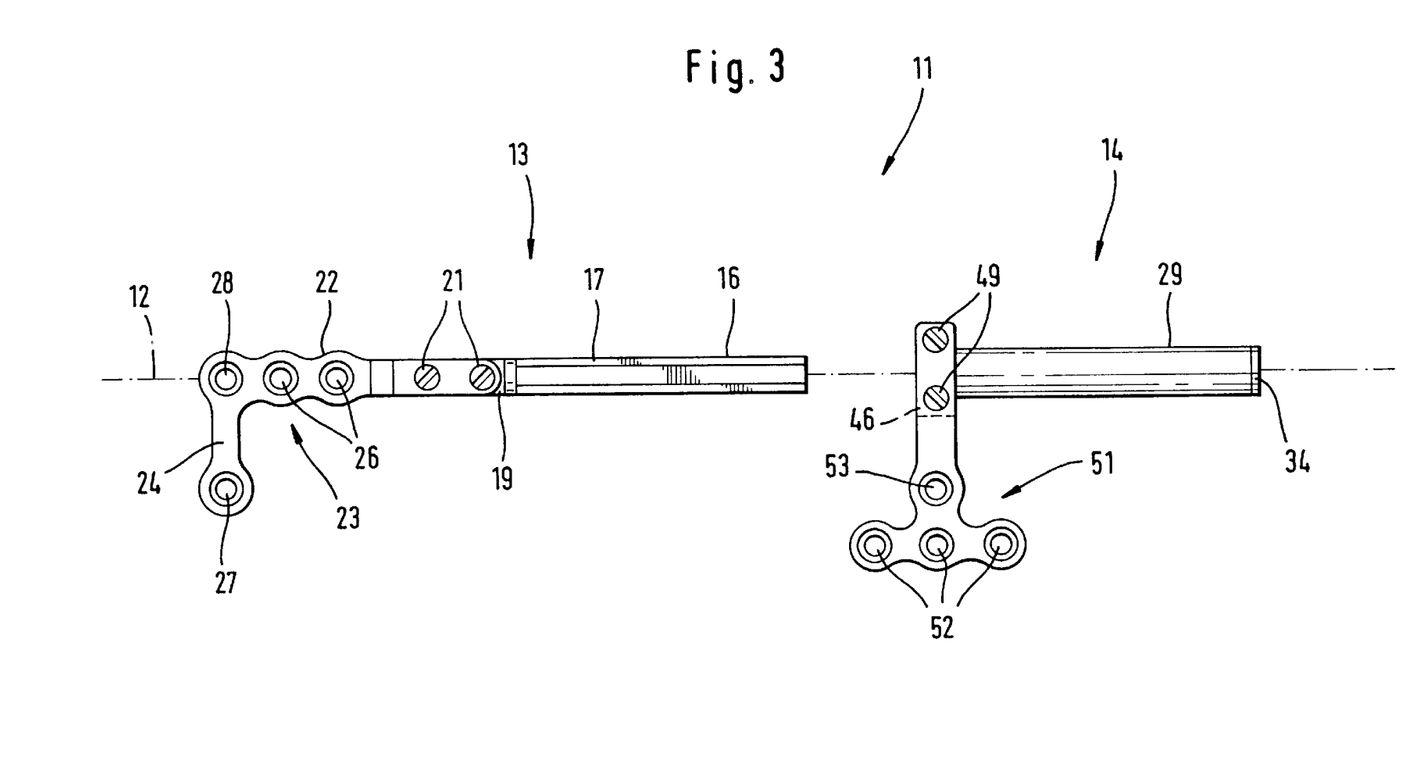
FIG. 3 shows the device according to FIG. 2, but in the partially exploded state.
Figure 5:
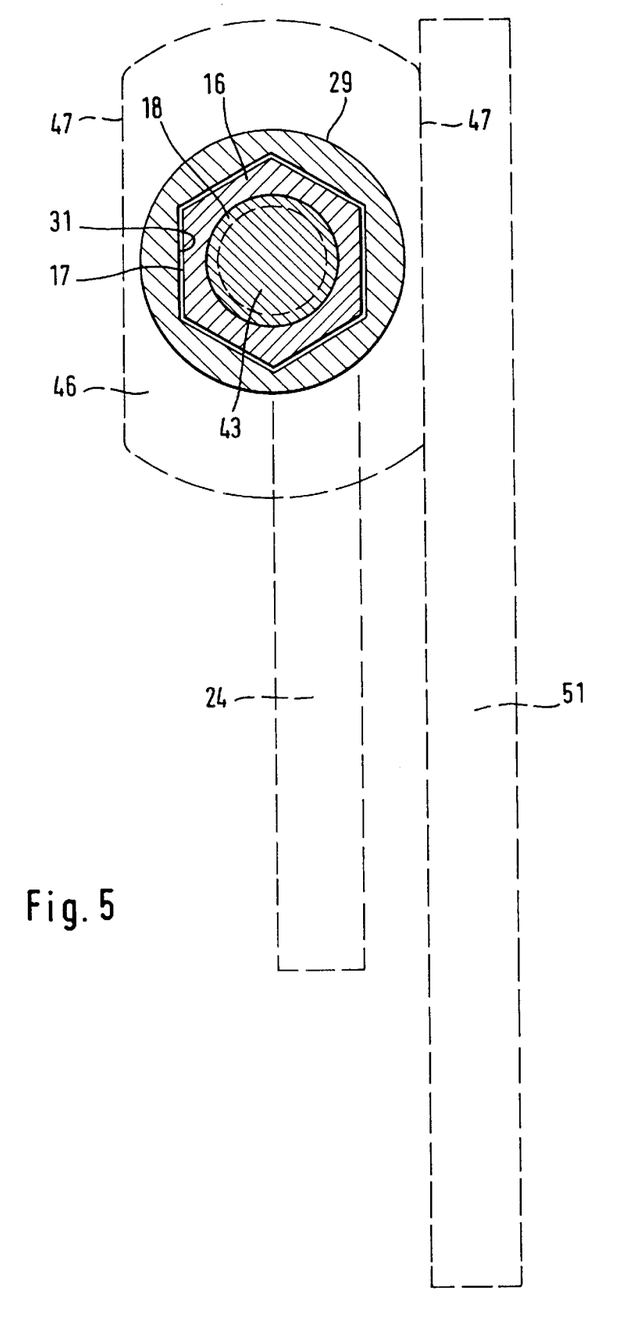
FIG. 5 shows a section along the line 5—5 in FIG. 2 in a considerably enlarged depiction.
Figure 6:
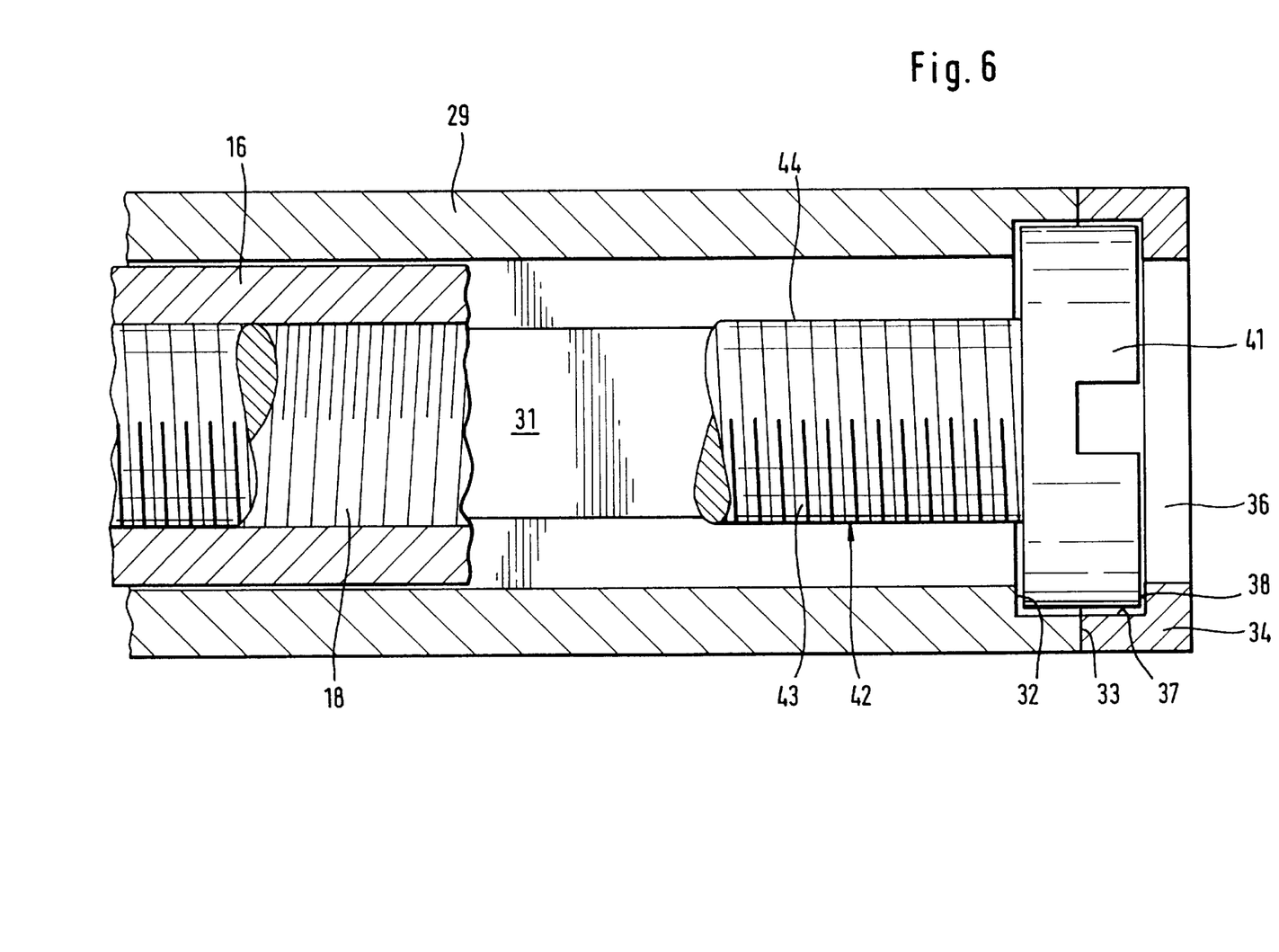
FIG. 6 shows a radial section through the right-hand end region of FIG. 3.

A small metal block 46 is located in the left-hand end region of the sleeve 29, and is firmly connected to the sleeve 29, permits the hexagonal rod 16 to pass through in a central hole, and has respective flats 47 on the two sides. Two threaded through holes 48 are bored through the metal block 46. The fastening end of a T-piece 51 is screwed with two screws 49 to the respective appropriate flat 47; the T-piece 51 has fastening holes 52, likewise arranged in a T-shape, and a fastening hole 53, arranged in the transverse direction, through which holes bone screws can be turned.

Figure 4:
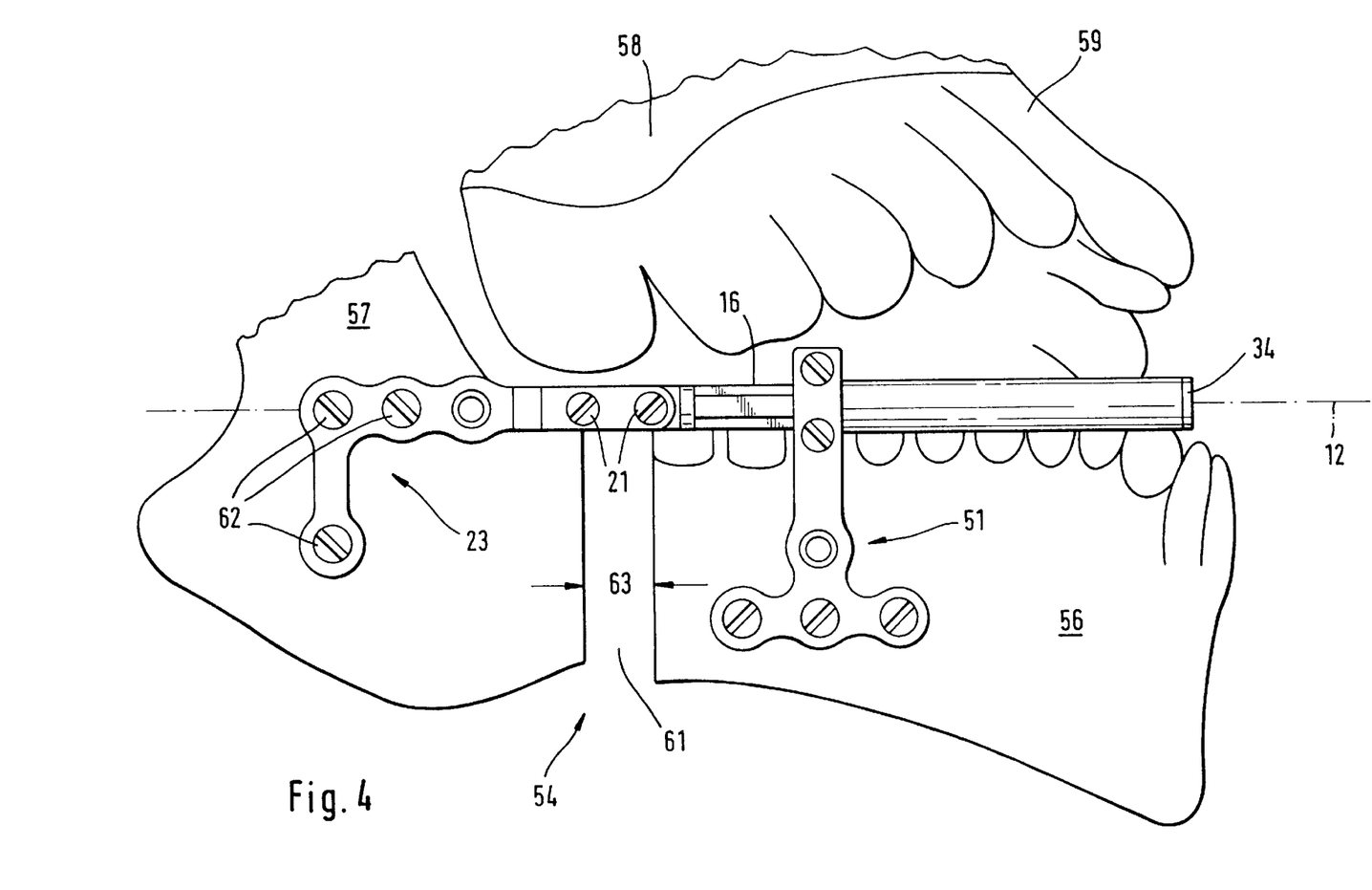
FIG. 4 shows the device according to FIG. 2 or 3, fitted to the inside of the left lower jaw ramus.

According to FIG. 4, a left lower jaw 54 has a horizontal ramus 56 and a rising ramus 57. The upper jaw 58 with its teeth 59 is also shown for orientation. The ramus 56 was separated by a cut 61, and to the left of it the angle piece 23 was fastened with screws 62, so that thrust forces and moment forces could be taken up. The T-piece 51 was fastened to the right-hand portion of the ramus 56, so that thrust forces and moment forces could be transmitted. The angle piece 23 and the T-piece 51 were fastened directly to the bone. The hexagonal rod 16 has already extended nearly half way. The cap 34 is located at a place within and behind the left corner of the mouth, so that nothing at all of the device 11 is seen when the mouth is closed.

A compression spring can also be provided as a force accumulator within the device, for example between the head 41 and the recess 32, so that the dilation force is delivered over a longer period of time.

The internal space of the sleeve 29 would alternatively have space sufficient space for an electric micro-motor, which would rotate slowly as a low voltage motor, and thus push the hexagonal rod 16 or an equivalent part out of the sleeve 29.

There would also be space for a hydraulic or pneumatic force accumulator, which would likewise deliver its force in a regulated manner over a longer period of time, where the pressure in the force accumulator is built up once, e.g. with compressive fluid, and then acts over a longer period of time.

Figure 7:
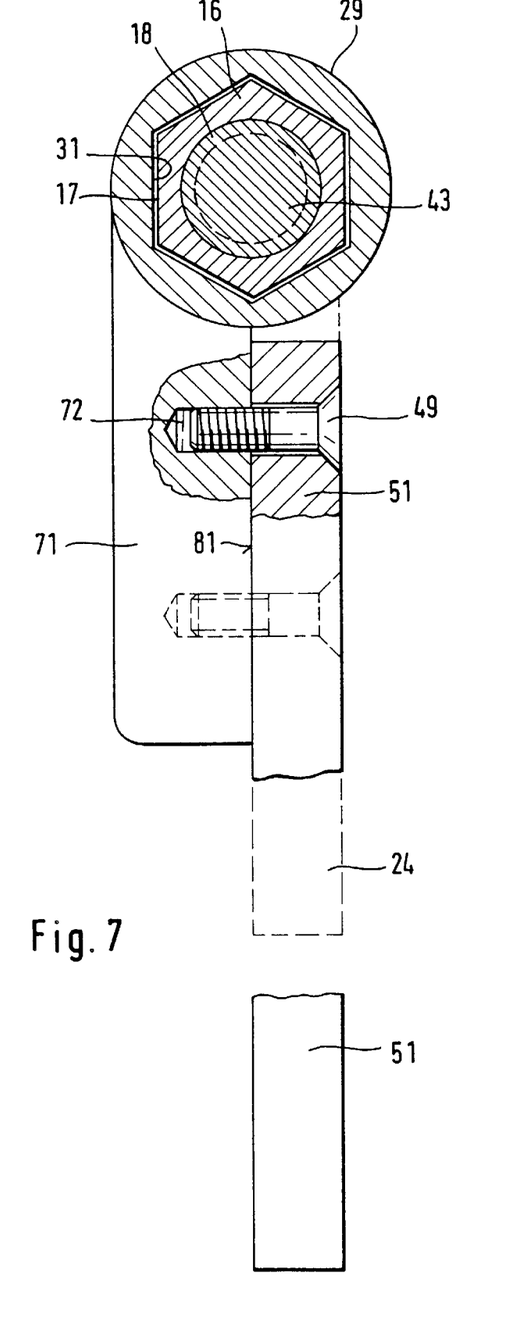
FIG. 7 shows a section, analogous to the line 5—5 in FIG. 2, of an alternative device for the right jaw ramus.

An alternative embodiment of a device 11 is shown in FIG. 7. A difference from the device shown in FIGS. 1–6 is the provision, instead of the small metal block 46 in FIG. 5, of a seat 71 which is formed directly on the sleeve 29. This seat 71 is constructed as an arm which runs essentially perpendicular to the longitudinal axis 12 of the sleeve 29. A seating surface 81 for the arrangement of the plate 51 is thereby constructionally arranged such that the seated plate 51 lies in essentially the same plane as the leg 24, which is arranged on the half 13 by means of an angle piece 23 and a leg 22. The plate 51 is likewise arranged on the seat 71 by means of two screws 49, which are advantageously formed as countersunk-head screws, at bores 72 to the seat 71.

This arrangement has the advantage that it can confer a considerable reduction in the constructional size. Moreover, this arrangement has the advantage that simple handling is conferred by the plate 51 and leg 24 lying in one plane. A deformation, due to which material fatigue can later enter in, of at least the plate 51 in order to fit the device 11 to a ramus of a jaw, can be made smaller. Moreover, such an embodiment of the device is gentler for the implant.

The remaining components of this device 11 correspond to the distraction device described in FIGS. 1–6. Likewise, an adjusting device described in FIGS. 8 and 9 can be arranged on the device 11 described in FIG. 6.

Figure 8:
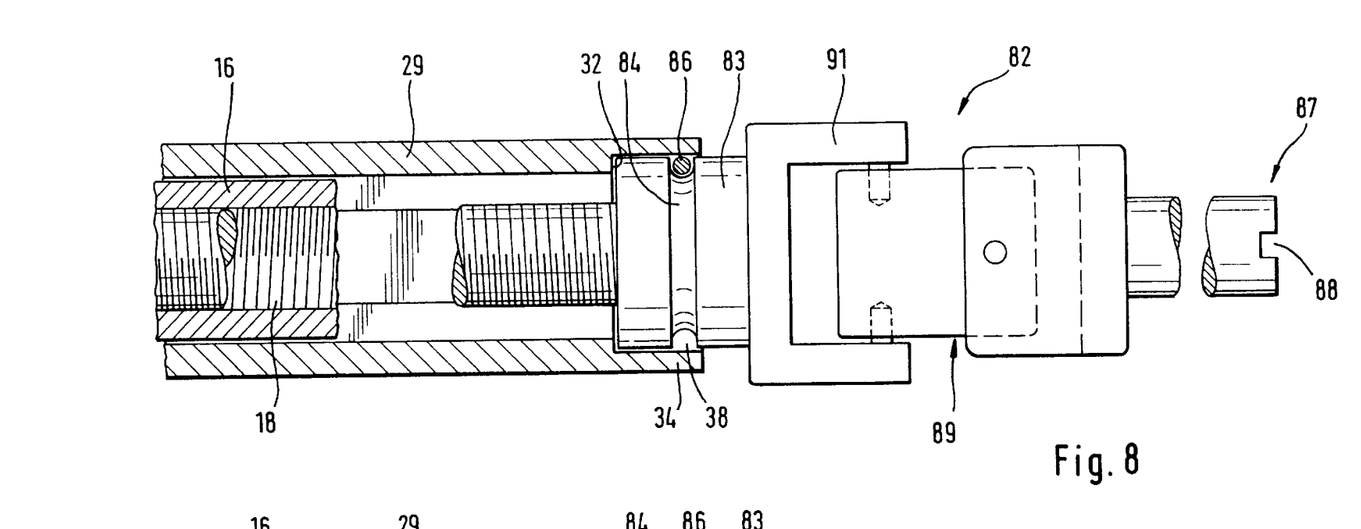
FIG. 8 shows a partial radial section through the right-hand end region of FIG. 3 in an advantageous development.

An alternative embodiment of a device 11 according to FIGS. 1–6 is shown in FIG. 8. This device 11 can preferably be arranged on the rising lower jaw ramus. However, this device 11 also offers advantages on the horizontal ramus 56, 57 for correspondingly unfavorable anatomical circumstances.

The device 11 has an adjusting device 82 for the adjustment of the distance between a rear and a front section of a ramus of the lower jaw. This adjusting device 82 has a guide section 83 adjoining the internal thread 18 and guided in an end region 34 of the sleeve 29. The guide section 83 has a semicircular recess 84, to which a pin 86 is arranged tangentially in the end region 34, in order to dispose the guide section 83 in the internal space 38 formed by the internal recess 82, and to secure the internal thread 18 axially. Alternatively, it can also be provided that a rectangular recess 84 is provided on the guide section 83. Furthermore, alternative constructions for axial securement can be provided. The guide section 83 projects from the free end region 34 and has at its free end a tool seat 87. A slot 88 is provided to receive a screwdriver, and forms the tool seat 87. Alternatively, it can be provided here that the tool seat can be constructed as a crossed slot, internal or external hexagon, or for further kinds of tools.

An articulation 89 is provided between the guide section 83 and the tool seating 87, making possible an adjustment of the device 11 when setting the device 11 in place on a rising ramus of the lower jaw, making it possible to introduce the tool through the oral cavity. An incision in the cheek for the introduction of a screwdriver, required with the devices heretofore when used on a rising ramus, is thereby avoided. The articulation 89 is movable, at least to a small degree, out of the geometrical longitudinal axis 12 of the device 11. It can be constructed, for example, as a ball joint, Cardan joint, or the like. The articulation 89 is advantageously made very small, so that the fork 91 arranged on the guide section 83 to receive the articulation 89 essentially corresponds in diameter to the sleeve 29 of the half 14, or is made only slightly larger.

Figure 9:
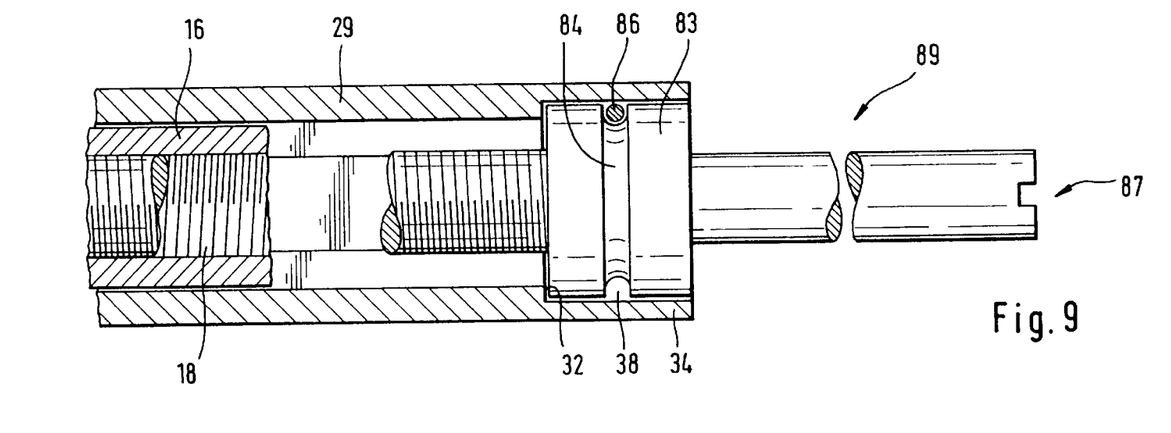
FIG. 9 shows a partial radial section through the right-hand end region of FIG. 3 in a further advantageous development.

An embodiment of an adjusting device 82 which is an alternative to the device shown in FIG. 8 is shown in FIG. 9. The articulation 89 is constructed as a flexible shaft. This can, for example, be constructed as a wire spiral, a wire cable which is twisted against the direction of rotation, or as a spring wire. A sleeve can advantageously be fitted around with wire spiral or the wire cable, in order to give the flexible shaft a certain torsional rigidity. Moreover, further embodiments for the construction of a flexible shaft can be provided, which can consist, for example, of flexible combinations of materials in order to transmit to the adjusting device 82 the torque applied by the tool to the tool seat 87, so that the first half 13 is movable relative to the second half 14. The end region 34 of the sleeve 29 can advantageously surround the whole guide section 83, by which means the guiding and the reception of force during the adjustment process can be heightened.

The device 11 can also be provided with a gearing, alternatively to the adjusting devices 82 described in FIGS. 8 and 9. Bevel wheels can then be used, which dispose the tool seat 87 in certain gradations of degrees to the geometrical longitudinal axis 12 of the device.

Furthermore, it can be provided that the tool seat 87 is arranged directly on the guide section 83, so that, for example, the articulation 89 is arranged on a tool which can be plugged onto the tool seat 87 which is arranged fixed to the internal thread 18.

Figure 10:
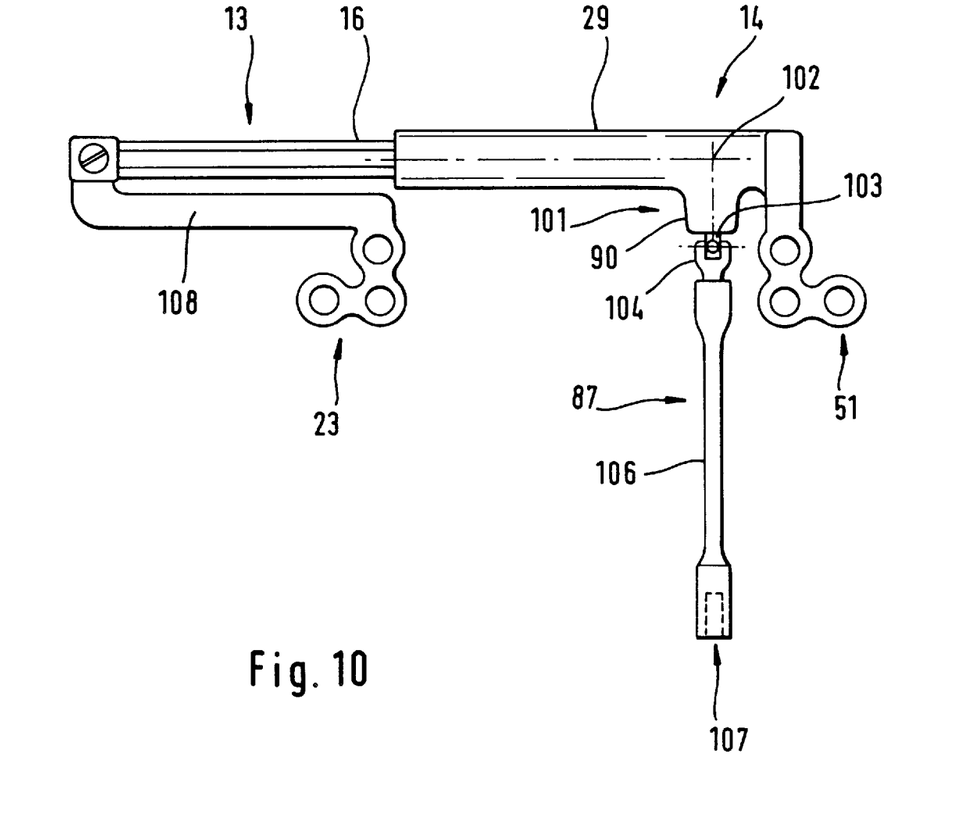
FIG. 10 shows a plan view of a further device with an adjusting device according to the invention in a maximum distraction position.

A further alternative embodiment of a distraction device is shown in FIG. 10, in which the adjusting device 101 is arranged between the fixing devices 23, 51. The adjusting device 101 has an articulation 102 arranged in the sleeve 29 of the first half 14. One outlet of this articulation 102 engages the half 13; the second outlet of the articulation 102 is constructed as a drive rod 103. The sleeve 29 has a guide section 90, which is formed on the sleeve 29, for fixing and guiding the drive rod 103. The articulation 102 is constructed as bevel wheel gearing. Alternatively, further kinds of gearing, for example, worm wheel gearing, are used, which fulfill the function that a drive axis of a drive rod 103 is arranged to deviate from a longitudinal axis 12 of the device 11. The gear ratios of the articulation used can be matched to the respective case of application, so that a simple and precise distraction of the bones can be given by the halves 13 and 14.

A joint 104 is arranged outside the guide section 90, and receives an extension 106. A tool key (not shown) can be applied to a seat 107 at the free end of the extension 106. An actuation of the articulation 102 can thereby be given in different angular positions relative to the drive rod 103.

It can also be provided that the extension 106 is constructed to be removable from the joint 104.

A further alternative embodiment of the invention has a drive rod 103 with a tool seat 107 which is provided on the end opposite to the articulation 102. The tool seat 107 is constructed such that this is simultaneously constructed as a seat for a joint 104 or an extension 106.

The joint 104 and/or the extension 106 can thus be positionable relative to the drive rod 103 according to the application.

The construction of the guide section 90 on the sleeve 29 is arranged in the plane of the fixing devices 23, 51, according to the embodiment example. Alternatively, it can be provided that for given cases of application the guide section 90 can be arranged, deviating from the arrangement shown in FIG. 10, on the sleeve 29, distributed on the periphery. Thus, for example, the guide section can be formed on the sleeve 29, turned by 180° around the longitudinal axis 12.

Likewise, for example, analogous embodiments according to FIGS. 1–3, 6, 8 and 9 can be constructed at the second outlet of the articulation 102.

The half 13 has an n-sided external cross section, which is preferably constructed as an external square section bar 16 and essentially corresponds to the length of the half 14, so that this can be fully inserted. A holding element 108 is arranged, parallel to the external square section bar 16, at the free end of the half 13, and carries the fixing device 23. This arrangement makes it possible for the fixing devices 23 and 51 to be positioned lying close to each other, with the exception of the region for the articulation 102 or the guide section 90, when the external square section bar 16 of the half 13 is inserted into the sleeve of the half 14.

Figure 1:
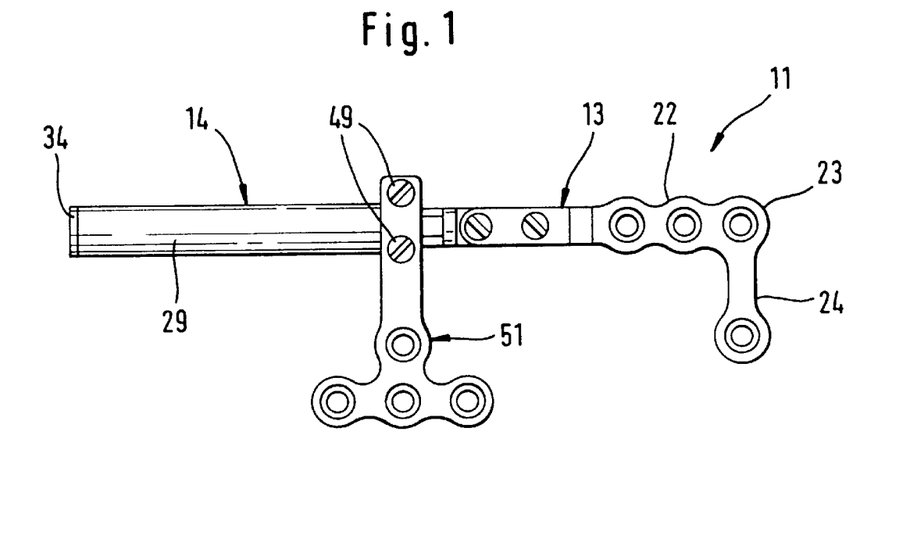
FIG. 1 shows, to scale, a plan view of a device for the right jaw ramus, seen from within the oral cavity.
Figure 2:
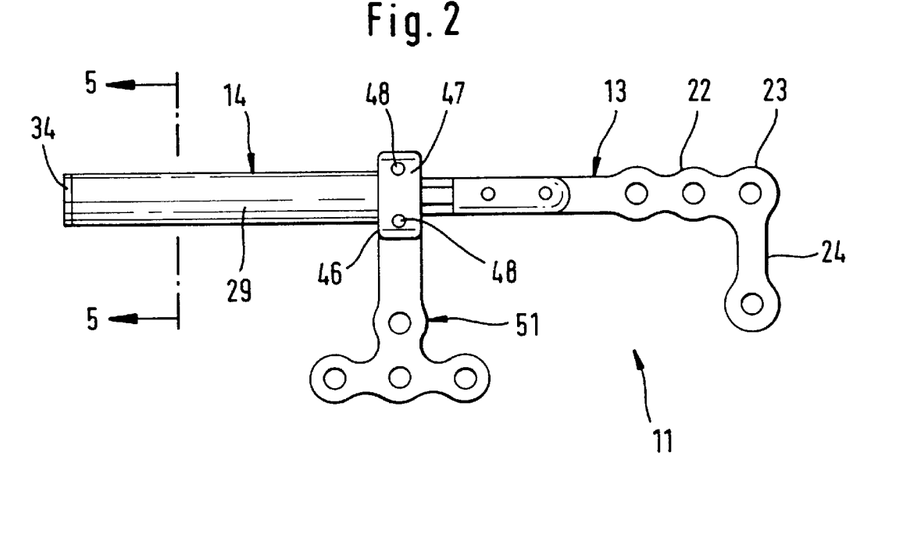

The integration of the articulation 102 into the sleeve can likewise be provided in the embodiments according to FIGS. 1–3, and can be carried over to further special embodiments of the mountings.

Furthermore, the advantageous embodiments and arrangements of FIGS. 1–9 can likewise be carried over, in optional combination with each other, to an embodiment according to FIG. 10.

We claim:

1. Device for distraction of at least two bone segments, with mountings which are displaceable relative to each other, for the distraction of bone segments in the jaw, face and skull region, in which a mounting (11) has an at least geometrical and at least substantially linear longitudinal axis (12), along which two complementary halves (13, 14) are adjustably movable by an adjusting device (41, 43, 16, 18; 82), with an increase of their mutual distance (63), the mounting (11) is longer than it is wide, the halves are guided for longitudinal movement on each other by a guide (17, 31) which is secured against twisting, on each half (13, 14), at least one flat fixing device (23, 51) is provided, which can be fixed to a bone (56, 57) and which can take up thrust forces and torques, the adjusting device (41, 43, 16, 18; 82) is accessible at a place for an adjusting member (42), which is directed towards a bodily orifice, the adjusting device (82) on one half (14) includes a sleeve (29) with a free end region (34) that is at least partially opens a guide section (83) that is rotatably mounted in this end region (34), and outside the end region (34) a tool seat (87) arranged on the guide section (83).

2. Device according to claim 1, in which the adjusting device (41, 43, 18; 82) includes at least one internal thread (18) and a self-locking external thread (44), which lie at least substantially parallel to the geometrical longitudinal axis (12).

3. Device according to claim 2, in which the internal thread (18) and the external thread (44) lie on the geometrical longitudinal axis (12).

4. Device according to claim 1, in which the adjusting device (41, 43, 18; 82) has a force storing element which produces a thrust.

5. Device according to claim 1, in which the adjusting device (41, 43, 18) has a micro electric motor.

6. Device according to claim 1, in which the adjusting device (41, 43, 18) has a fluid pressure device.

7. Device according to claim 1, in which the guide (17, 31) which is secured against twisting includes two telescopically mutually interfitting non-round members (17, 31).

8. Device according to claim 7, in which the non-rounded members (17, 31) are an internal polygonal section body (31) and an external polygonal section body (17).

9. Device according to claim 1, in which a head (41) of a screw (42) is rotatable in this end region (34), and is guided at least substantially immovably in the axial direction (12); the sleeve (29) is open at its other end and has a coaxial internal polygonal section body (31) accessible from there; the other half has an external polygonal section body (31); and the external polygonal section body (17) includes an internal threaded bore (18) into which a shaft (43) of the screw (42) is inserted.

10. Device according to claim 1, in which the fixing device (23, 51) includes osteosynthesis plates (23, 51).

11. Device according to claim 10, in which the plates are maxi-plates.

12. Device according to claim 10, in which the plates are mini-plates.

13. Device according to claim 10, in which the plates are micro-plates.

14. Device according to claim 10, in which the plates are angle plates (23).

15. Device according to claim 10, in which the plates are T-plates (51).

16. Device according to claim 1, in which an angle plate is provided in an end region (19) of the adjusting device.

17. Device according to claim 1, in which a T-plate is provided in an end region (19) of the adjusting device.

18. Device according to claim 1, in which the tool seat (87) can be positioned in an angular position which deviates from the longitudinal axis (12).

19. Device according to claim 1, in which an articulation (89) is provided between the guide section (83) and the tool seat (87).

20. Device according to claim 19, in which the articulation (89) comprises a Cardan joint.

21. Device according to claim 19, in which the articulation (89) is comprises a ball joint.

22. Device according to claim 19, in which the articulation (89) is comprises a flexible shaft.

23. Device according to claim 19, in which the articulation (89) comprises a bevel gearing.

24. Device according to claim 1, in which the sleeve (29) has a seat (71) formed on the sleeve (29) to receive the fixing device (51).

25. Device according to claim 24, in which the seat (71) is arranged substantially at right angles to the longitudinal axis of the sleeve (29).

26. Device according to claim 24, in which the seat (71) has a fastening element (72) to which the fixing device (51) can be fastened.

27. Device according to claim 24, in which the seat is formed on the sleeve (29) in such a manner that the fixing devices (23, 51) can be arranged in a common plane.

28. Device according to claim 1, in which a left-hand and a right-hand adjusting device for the left and right ramus of the jaw are provided.

29. Device for distraction of at least two bone segments, with mountings which are displaceable relative to each other, for the distraction of bone segments in the jaw, face and skull region, in which a mounting (11) has an at least geometrical and at least substantially linear longitudinal axis (12), along which two complementary halves (13, 14) are adjustably movable by an adjusting device (41, 43, 16, 18; 82), with an increase of their mutual distance (63), the mounting (11) is longer than it is wide, the halves are guided for longitudinal movement on each other by a guide (17, 31) which is secured against twisting, on each half (13, 14), at least one flat fixing device (23, 51) is provided, which can be fixed to a bone (56, 57) and which can take up thrust forces and torques, the adjusting device (41, 43, 16, 18; 82) is accessible at a place (36) for an adjusting member (42), which is directed towards a bodily orifice, the adjusting device (101) has a tool seat (87) arranged between the fixing devices (23, 51), and the tool (87) can be positioned in an angular position which deviates from the longitudinal axis (12).

30. Device according to claim 29 in which a right-hand adjusting device is provided for a respective horizontal (56) and rising (57) ramus of the jaw.

31. Device according to claim 29, in which the adjusting device (101) has a guide section (90) which deviated from the geometrical longitudinal axis (12), for guiding a drive rod (103) of an articulation (102).

32. Device according to claim 31, in which the articulation (102) comprises an angle gearing.

33. Device according to claim 31, in which the drive rod (103) has a joint (104) outside the guide section (90).

34. Device according to claim 33, in which an extension (106) with a tool seat (107) is arranged on the joint (104).

35. Device according to claim 34, in which the drive rod (103), the joint (104), and the extension (106) are formed integrally.

36. Device according to claim 35, in which the joint (104) and the extension (106) are arranged releasably with respect to the drive rod (103).

37. Device according to claim 31, in which the guide section (90) is arranged in a plane of the fixing devices.

38. Device according to claim 29, in which a half (13) has a section (108) which runs essentially parallel to the half, and receives a fixing device at one end.

39. Device according to claim 29, in which a left-hand and right-hand adjusting device is provided for a left and right jaw ramus.

* * * * *